(12) United States Patent
Bracken et al.

(10) Patent No.: US 11,850,083 B2
(45) Date of Patent: Dec. 26, 2023

(54) DEVICE FOR MODIFYING AN IMAGING OF A TEE PROBE IN X-RAY DATA

(71) Applicant: KONINKLIJKE PHILIPS N.V., Eindhoven (NL)

(72) Inventors: John Allan Bracken, Denver, CO (US); Niels Nijhof, Ultrecht (NL); Michael Grass, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1278 days.

(21) Appl. No.: 15/310,995

(22) PCT Filed: May 5, 2015

(86) PCT No.: PCT/EP2015/059821
§ 371 (c)(1),
(2) Date: Nov. 14, 2016

(87) PCT Pub. No.: WO2015/173069
PCT Pub. Date: Nov. 19, 2015

(65) Prior Publication Data
US 2017/0079600 A1    Mar. 23, 2017

(30) Foreign Application Priority Data

May 16, 2014   (EP) .................................... 14168562

(51) Int. Cl.
*A61B 6/12*     (2006.01)
*A61B 6/00*     (2006.01)
(Continued)

(52) U.S. Cl.
CPC .............. *A61B 6/12* (2013.01); *A61B 6/4441* (2013.01); *A61B 6/461* (2013.01); *A61B 6/463* (2013.01);
(Continued)

(58) Field of Classification Search
None
See application file for complete search history.

(56) References Cited

U.S. PATENT DOCUMENTS

| 10,238,361 B2 | 3/2019 | Gogin et al. |
| 2005/0049486 A1 | 3/2005 | Urquhart et al. |

(Continued)

FOREIGN PATENT DOCUMENTS

| DE | 102010062340 A1 | 6/2012 |
| DE | 102012215001 A1 | 2/2014 |

(Continued)

OTHER PUBLICATIONS

Lang et al., "Three-Dimensional Ultrasound Probe Pose Estimation from Single-Perspective X-Rays for Image-Guided Interventions", MIAR 2010, LNCS 6326, pp. 344-352. (Year: 2010).*

(Continued)

*Primary Examiner* — Katherine L Fernandez

(57) ABSTRACT

The present invention relates to a device (1) for modifying an imaging of a TEE probe in X-ray data, a medical imaging system (100) for modifying an imaging of a TEE probe in X-ray data, a method for modifying an imaging of a TEE probe in X-ray data, a computer program element for controlling such device (1) and a computer readable medium having stored such computer program element. The device (1) comprises an X-ray data provision unit (11), a model provision unit (12), a position locating unit (13), and a processing unit (14). The X-ray data provision unit (11) is configured to provide X-ray data comprising image data of a TEE probe. The model provision unit (12) is configured to provide model data of the TEE probe. The position locating unit (13) is configured to locate a position of the TEE probe in the X-ray data based on the model data of the TEE probe. The processing unit (14) is configured to define a region in a predetermined range adjacent to the TEE probe as refer- (Continued)

ence area. The processing unit (14) is configured to process the X-ray data of the reference area into estimated X-ray data of a region occupied by the TEE probe. The processing unit (14) is configured to modify the X-ray data in the region occupied by the TEE probe based on the estimated X-ray data.

20 Claims, 3 Drawing Sheets

(51) Int. Cl.
*A61B 8/12* (2006.01)
*G06T 5/00* (2006.01)
*G06T 7/00* (2017.01)
*A61B 8/00* (2006.01)

(52) U.S. Cl.
CPC .............. *A61B 6/467* (2013.01); *A61B 6/503* (2013.01); *A61B 6/5235* (2013.01); *A61B 6/5252* (2013.01); *A61B 6/5258* (2013.01); *A61B 8/12* (2013.01); *G06T 5/008* (2013.01); *G06T 7/0012* (2013.01); *A61B 8/445* (2013.01); *G06T 2207/10116* (2013.01); *G06T 2207/30048* (2013.01); *G06V 2201/034* (2022.01)

(56) References Cited

U.S. PATENT DOCUMENTS

| | | | |
|---|---|---|---|
| 2010/0268067 A1 | 10/2010 | Razzaque et al. | |
| 2011/0123074 A1* | 5/2011 | Nie | G06T 5/008 |
| | | | 382/128 |
| 2012/0143045 A1 | 6/2012 | Klingenbeck | |
| 2012/0163686 A1 | 6/2012 | Liao et al. | |
| 2012/0237115 A1 | 9/2012 | Rohkohl | |
| 2012/0245458 A1* | 9/2012 | Gogin | A61B 6/00 |
| | | | 600/424 |
| 2013/0023766 A1* | 1/2013 | Han | A61B 6/5264 |
| | | | 600/427 |
| 2013/0060132 A1* | 3/2013 | Liao | A61B 6/12 |
| | | | 600/431 |
| 2013/0324839 A1 | 12/2013 | Chien | |
| 2015/0294454 A1* | 10/2015 | Nempont | G06T 7/30 |
| | | | 382/128 |

FOREIGN PATENT DOCUMENTS

| | | |
|---|---|---|
| JP | 2001238959 A | 9/2001 |
| WO | 200000086 A1 | 1/2000 |
| WO | 20130144912 A1 | 10/2013 |

OTHER PUBLICATIONS

Skifstad, "Intensity Gradient Analysis", High-Speed Range Estimation Based on Intensity Gradient Analysis, Springer Series in Perception Engineering, Springer, New York, pp. 45-54, 1991. (Year: 1991).*
Merriam-Webster, "Definition of Gradient", https://www.merriam-webster.com/dictionary/gradient, accessed on Apr. 16, 2021.*
Lang, P. et al "US Fluoroscopy Registration for Transcatheter Aortic Valve Implantation" IEEE Transactions on Biomedical Engineering, vol. 59, No. 5, May 2012.
Hatt, Charles R. et al. "Efficient feature-based 2D/3D registration of transesophageal echocardiography to x-ray fluoroscopy for cardiac interventions" Proc. SPIE 9036, Medical Imaging, 2014—Abstract Only.
Mountney, Peter et al. "Ultrasound and Fluoroscopic Images Fusion by Autonomous Ultrasound Probe Detection", MICCAI 2012, PART 11, LNCS 7511, pp. 544-551.

* cited by examiner

DEVICE FOR MODIFYING AN IMAGING OF A TEE PROBE IN X-RAY DATA

CROSS-REFERENCE TO PRIOR APPLICATIONS

This application is the U.S. National Phase Application under 35 U.S.C. § 371 of International Application No. PCT/EP2015/059821, filed on May 5, 2015, which claims the benefit of European Patent Application No. 14168562.8, filed on May 16, 2014. These applications are hereby incorporated by reference herein.

FIELD OF THE INVENTION

The present invention relates to a device for modifying an imaging of a TEE probe in X-ray data, a medical imaging system for modifying an imaging of a TEE probe in X-ray data, a method for modifying an imaging of a TEE probe in X-ray data, a computer program element for controlling such device and a computer readable medium having stored such computer program element.

BACKGROUND OF THE INVENTION

X-ray imaging (fluoroscopy and angiography) is an important imaging modality for cardiac interventions. For providing a guidance of procedures that require more soft-tissue information than provided by X-ray imaging, transesophageal echocardiography (TEE) information is employed. TEE imaging, which is a form of ultrasound imaging, is able to show an interventional device and its surrounding anatomy simultaneously and provides excellent detail of anatomical structure and function that is often lacking in live X-ray images.

US 2012/245458 A1 discloses to detect and track an intervention device in a 2D fluoroscopy image and to steer an ultrasound probe beam towards this device. The ultrasound probe is registered in the fluoroscopy image and the registering includes the estimation of the position and of the orientation of the probe relative to the fluoroscopy.

DE 10 2012 215001 A1 discloses a method for two dimensional-three dimensional-registration of a three-dimensional model of an instrument. The method involves recording a roentgen-gram in a cone-beam geometry, where groups associated to a sub-step are used by less than six transformations of a model. The associated group, in each transformation parameter, is optimized iterative with the roentgen-gram in its actual considered position by comparison of forward projection of the model corresponding to the imaging geometry of the roentgen-gram.

US 2011/123074 A1 discloses a system and method for altering the appearance of an artificial object in a medical image. An artificial object is first identified in the medical image, such as identifying a breast implant in a mammography image. The prominence of the artificial object is then reduced, for example by suppressing the brightness or masking the artificial object out altogether.

During complex cardiac interventions in a cath lab, such as transcatheter aortic valve replacements (TAVR) or other structural heart disease interventions, TEE imaging is often used as a complementary imaging modality to the live X-ray imaging to help guide and assess the procedure. However, live X-ray is used as the workhorse imaging modality for catheter and device guidance and for vascular imaging during these procedures. When using TEE, an imaging probe is e.g. inserted into the esophagus of the patient at a position that is behind the heart. This TEE probe shows up very clearly in live X-ray images.

The problem with the TEE probe being visualized so clearly in the X-ray images is that it often gets in the way of or obstructs the anatomy and devices that the interventional cardiologist wants to be able to see in the live X-ray images during a procedure.

As a result of such obstructions, the interventional cardiologist will often have to ask the echocardiographer to move the TEE probe out of the way during various stages of a procedure. Then, the echocardiographers will no longer be able to see the TEE images that they want to see after doing this. This means that echocardiographers will have to move the probe back into position a little bit later in the procedure to be able to resume their desired visualization of the structures they want to be able to see in the TEE images.

This whole process is disruptive to the clinical workflow and time consuming for both interventional cardiologists and echocardiographers. It is riskier for the patient as well, since this additional motion and adjustment of the TEE probe within the esophagus could put the patient at some additional risk.

SUMMARY OF THE INVENTION

Hence, there may be need to provide a device for modifying an imaging of a TEE probe in X-ray data, which is easier to handle.

The object of the present invention is solved by the subject-matters of the independent claims, wherein further embodiments are incorporated in the dependent claims. It should be noted that the following described aspects of the invention apply also for the a device for modifying an imaging of a TEE probe in X-ray data, for the medical imaging system for modifying an imaging of a TEE probe in X-ray data, for the method for modifying an imaging of a TEE probe in X-ray data, for the computer program element, and for the computer readable medium.

According to the present invention, a device for modifying an imaging of a TEE probe in X-ray data is presented. The device comprises an X-ray data provision unit, a model provision unit, a position locating unit, and a processing unit. The X-ray data provision unit is configured to provide X-ray data comprising image data of a TEE probe. The model provision unit is configured to provide model data of the TEE probe. The position locating unit is configured to locate a position of the TEE probe in the X-ray data based on the model data of the TEE probe. The processing unit is configured to define a region in a predetermined range adjacent to the TEE probe as reference area. The processing unit is configured to process the X-ray data of the reference area into estimated X-ray data of a region occupied by the TEE probe. The processing unit is configured to modify the X-ray data in the region occupied by the TEE probe based on the estimated X-ray data.

The device for modifying an imaging of a TEE probe in X-ray data according to the present invention enables interventional cardiologists to visualize the desired structures and devices that they wish to see in the live X-ray images without the echocardiographer having to move the TEE probe out of the way. With this approach, the echocardiographer will not have to reposition the probe to resume visualization of the desired structures in the TEE images. As a result, the device for modifying an imaging of a TEE probe in X-ray data is easier to handle.

In an example, the device for modifying an imaging of a TEE probe in X-ray data according to the present invention enables interventional cardiologists to temporarily modify, e.g. to make translucent, to hide and/or to conceal, the TEE probe in the X-ray images without having to move the probe. This enables echocardiographers to continue to visualize structures of interest in the TEE images without interruption, and enables the interventional cardiologists to see the desired structures and devices of interest in the live X-ray images. As a result, the device for modifying an imaging of a TEE probe in X-ray data improves the clinical workflow and reduces the risk for the patient.

In an example, the modification of the X-ray data in the region occupied by the TEE probe comprises a hiding of the TEE probe, a translucent or transparent imaging of the TEE probe and/or a reduction to an outline of the TEE probe. The translucent or transparent imaging and/or the reduction to an outline may be implemented with a color and/or grey scale to indicate a parameter of interest. Also opacity of the TEE probe in the images can be varied, e.g. depending on TEE probe parameters, as e.g. temperature, pressure, torsion of the various regions/surfaces of the TEE probe etc.

For example, it is possible to show the TEE probe as an outline or a slightly transparent surface of the TEE probe in the X-ray images. This allows the TEE probe to be visualized without obstructing regions of interest in the live X-ray images. This TEE probe outline or its slightly transparent surface can be further adapted to show a TEE probe temperature or even pressure against a surface or anatomical structure in the patient as a colour scale, or to show position and/or orientation within the patient as a colour scale. It is further possible to switch between different colour scale metrics. It is also possible to adjust the degree of transparency of the model if a surface visualization is used to display the TEE probe. The TEE probe may also emit a field of view cone, which can be modelled and displayed overtop of the live X-ray images. This field of view cone can be modified to show a slightly transparent surface that can display colour scales that indicate different metrics of interest in e.g. the patient. The cone in this case can show a particular metric, e.g. temperature of the patient within the TEE probe's field of view.

In an example, the X-ray data of the reference area comprise X-ray data of a region around the position of the TEE probe and/or a region within an X-ray transparent portion of the TEE probe. In other words, besides to the background regions around the perimeter of the TEE probe, the TEE probe head may also have e.g. two X-ray transparent regions that can also be used to modify the TEE probe in the X-ray images. If a 3D geometry of the TEE probe head is known from a TEE probe model, the geometry of these X-ray transparent regions is also known. Therefore, these X-ray transparent regions can be pre-segmented ahead of time within the TEE probe model. These X-ray transparent regions and smaller sub-segments of them in the probe head can be used to modify the X-ray opaque part of the TEE probe head.

In an example, the modification of the X-ray data depends on a user input and/or a motion of an X-ray data acquisition unit and/or a motion of an object to be examined. In an example, the device for modifying an imaging of a TEE probe in X-ray data further comprises a control unit. The control unit may be configured to control the modification of the X-ray data in the region occupied by the TEE probe and/or to switch the modification on and off. The modification can also be amended according to the circumstances and/or the cardiologist's will.

For example, the device for modifying an imaging of a TEE probe in X-ray data according to the present invention enables interventional cardiologists to press a button and temporarily modify, e.g. make transparent, hide and/or conceal, the TEE probe in the live X-ray images such that they will then be able to see the structures and devices that were being blocked by the TEE probe. The invention may take advantage of X-ray transparent regions inside a TEE probe head and the image background regions around a perimeter of the TEE probe. Averages or gradients of these X-ray transparent regions can be used to block out the obstructing parts of the TEE probe such that structures crossing the TEE probe or hidden behind it can be visualized in a live X-ray run. It is also possible to use the present invention to hide the TEE probe during a C-arm rotational acquisition such that it is not present in a 3D reconstructed image volume generated after the acquisition. This could help to mitigate X-ray attenuation image artifacts that would normally be generated by the presence of the highly attenuating probe.

For example, the TEE probe can be concealed at a start of a rotational acquisition of an X-ray C-arm and then displayed again immediately after the rotational acquisition is complete. This allows a C-arm image projection data to be generated and reconstructed as a 3D image volume without the presence of the TEE probe in the projection images. The TEE probe concealment can be used to help mitigate X-ray attenuation streak artifacts in the reconstructed 3D volume caused by the presence of the TEE probe. Reconstructed 3D X-ray image volumes from a rotational acquisition of the X-ray C-arm provide additional anatomical details of the patient and can also be used as roadmaps to help guide interventional procedures.

In an example, the model provision unit is further configured to provide a 3D model of the TEE probe. The 3D model of the TEE probe can be e.g. 3D CAD model. For example, a computer model of the TEE probe head geometry is used to locate the position and orientation of the TEE probe in the live X-ray images. An automated search through the live X-ray images can be carried out to locate the TEE probe head position and orientation and the TEE probe model can automatically be registered to it. This defines the position, geometry and orientation of the TEE probe in the X-ray images for TEE probe modification. Once the position of the TEE probe is found in the X-ray images, image background regions around and within the probe may be extracted, averaged and interpolated and then overlaid on top of the TEE probe in each X-ray image frame to modify the image of the TEE probe in a live X-ray image run. This process may account for devices and contrast agents that can be present behind the TEE probe image. A button can be used on the interventional X-ray system that enables the interventional cardiologist to control the duration of TEE probe modification during a live X-ray run. Therefore, a modification algorithm can be used and activated across a live image sequence of multiple X-ray image frames. In an example, the TEE probe model can also be expanded to include a part of the TEE probe above the probe head as well.

In an example, it is possible to further improve the TEE probe model by augmenting it with the construction of a 3D model of TEE probe X-ray attenuation, such as from a CT scan. A previously generated CT scan of the TEE probe provides a 3D map of X-ray attenuation coefficients in the probe, and this attenuation model can be used to subtract out the TEE probe from the live X-ray projection images. This CT-based probe attenuation model provides an additional and improved signal and noise and image background information to remove the TEE probe effectively from the live X-ray images.

In an example, the position locating unit determines the TEE probe position in the X-ray images such that the TEE probe image modification algorithm can be implemented as follows. Once activated by the cardiologist, an automated search in the images may begin to locate the TEE probe position and orientation. A predesigned computer model of the probe may then be automatically aligned to the X-ray image of the TEE probe and this may help to determine the position and orientation of the TEE probe. This TEE probe position and orientation determination may occur automatically very quickly ($\approx$1s) over the course of a very small number of X-ray image frames. This probe alignment functionality may be used to register the X-ray and TEE images.

In an example, the position locating unit is configured to locate a position of a perimeter of the TEE probe in the X-ray data based on the model of the TEE probe. The processing unit may be configured to define subregions in a predetermined range adjacent to the perimeter of the TEE probe as reference areas, to process the X-ray data of the reference areas into estimated X-ray data of the subregions occupied by the TEE probe perimeter, and to modify the X-ray data of the subregions occupied by the TEE probe perimeter based on the estimated X-ray data. In an example, a subregion has a diameter or width corresponding approximately to a size of an interventional instrument to be used.

For example, to modify the perimeter of the TEE probe, small circular or elliptical subregions may be defined along the perimeter of the TEE probe, with a diameter of approximately the size of the smallest catheters typically used in interventional cardiology (e.g. 3F or 1 mm diameter). Since the position and orientation of the TEE probe is known from the TEE probe model being registered to the TEE probe image, these circular and elliptical subregions can be automatically generated around the TEE probe perimeter once the TEE probe modification algorithm is activated. By delineating circular/elliptical subregions on opposite sides of the TEE probe, a strip of image region with signal and noise levels that are the average of the two subregions can be overlaid across the TEE probe to modify it between the two circles or ellipses. These circles or ellipses may also interact with the sub-segments of regions on the TEE probe head to modify the TEE probe perimeter on the lower part of the TEE probe head. Finally, these circles or ellipses could interact with the region after it has been modified to modify the perimeter of the TEE probe around the region. By using a small enough circle/ellipse size, this ensures that catheters, guidewires and devices that cross in front of or behind the TEE probe remain visible in the X-ray images after the TEE probe has been modified, e.g. concealed.

In an example, the device for modifying an imaging of a TEE probe in X-ray data further comprises a determination unit. The determination unit may be configured to determine an average data signal and/or noise level of the X-ray data of the reference area. The determination unit may be further configured to assign the average data signal and/or noise level to the estimated X-ray data of the region occupied by the TEE probe.

In an example, the device for modifying an imaging of a TEE probe in X-ray data further comprises a determination unit configured to assign an intensity gradient to the estimated X-ray data of the region occupied by the TEE probe. For example, it is possible to set up an image intensity gradient between two regions to hide a part of the TEE probe instead of just using an average signal intensity and noise between the two regions. This approach helps to make transitions in image signal across parts of the TEE probe more gradual. This approach is helpful if a device, catheter or structure does not completely cross behind or in front of the TEE probe, but is still hidden by one side or part of the probe. The gradient approach still allows some of the device, catheter or structure to be displayed after hiding the TEE probe.

According to the present invention, also a medical imaging system for modifying an imaging of a TEE probe in X-ray data is presented. The medical imaging system comprises the device for modifying an imaging of a TEE probe in X-ray data, a TEE probe and an image acquisition device.

In an example, the TEE probe comprises a transparent portion arranged at an end of the TEE probe and/or at a beginning of a head of the TEE probe.

According to the present invention, also a method for modifying an imaging of a TEE probe in X-ray data is presented. The method comprises the following steps, not necessarily in this order:

a) providing X-ray data comprising image data of a TEE probe, b) providing model data of the TEE probe, c) locating a position of the TEE probe in the X-ray data based on the model data of the TEE probe, d) defining a region in a predetermined range adjacent to the TEE probe as reference area, e) processing X-ray data of the reference area into estimated X-ray data of a region occupied by the TEE probe, and f) modifying the X-ray data in the region occupied by the TEE probe based on the estimated X-ray data.

Exemplarily and in other words, the method for modifying an imaging of a TEE probe in X-ray data comprises two parts. First, use a previously generated 3D model of a TEE probe to subtract a TEE probe head out of live X-ray images. This 3D TEE probe model can be from a CAD design, a CT scan or even a C-arm scan and is registered to the live 2D X-ray images. With this 3D model approach, the C-arm can be rotated, a patient table can be moved, the TEE probe can also be moved, and the TEE probe is still be able to be removed from the live 2D X-ray images in real-time without having to constantly get new background digital subtraction angiography (DSA) images for subtraction, which helps to keep patient radiation doses low. The cardiologist can then use the 3D model to subtract out the TEE probe of the normal live X-ray images. Second, use a search/detection algorithm to find and remove the TEE probe from the live X-ray images directly, without having to acquire any extra background images first. In this way, no additional radiation is needed to acquire background images, the workflow is still smooth and the cardiologist can still use the standard X-ray images to guide e.g. the TAVR procedure.

The applications for the present invention are to prevent a TEE probe from obstructing catheters, devices and anatomical structures in live X-ray images used in interventional cardiology and to provide additional information about how the probe is interacting and performing in the patient. The applications may comprise structural heart disease interventions and transcatheter aortic valve replacement procedures. The modification/concealment/visualization technique can be a possible enhancement for existing C-arm X-ray systems or even a new feature in existing image guidance systems, which already use a geometric computer model of a TEE probe head. The TEE probe modification/concealment/visualization technique can be used with all TEE probes and also with pediatric TEE probes or intra-cardiac echocardiography probes.

In a further example of the present invention, an object tracking computer program for tracking a predetermined movable object is presented, wherein the computer program comprises program code means for causing a object tracking device as defined in the independent device claim to carry out the steps of the object tracking method as defined in the independent method claim, when the computer program is run on a computer controlling the object tracking device.

It shall be understood that the device for modifying an imaging of a TEE probe in X-ray data, the medical imaging system for modifying an imaging of a TEE probe in X-ray data, the method for modifying an imaging of a TEE probe in X-ray data, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
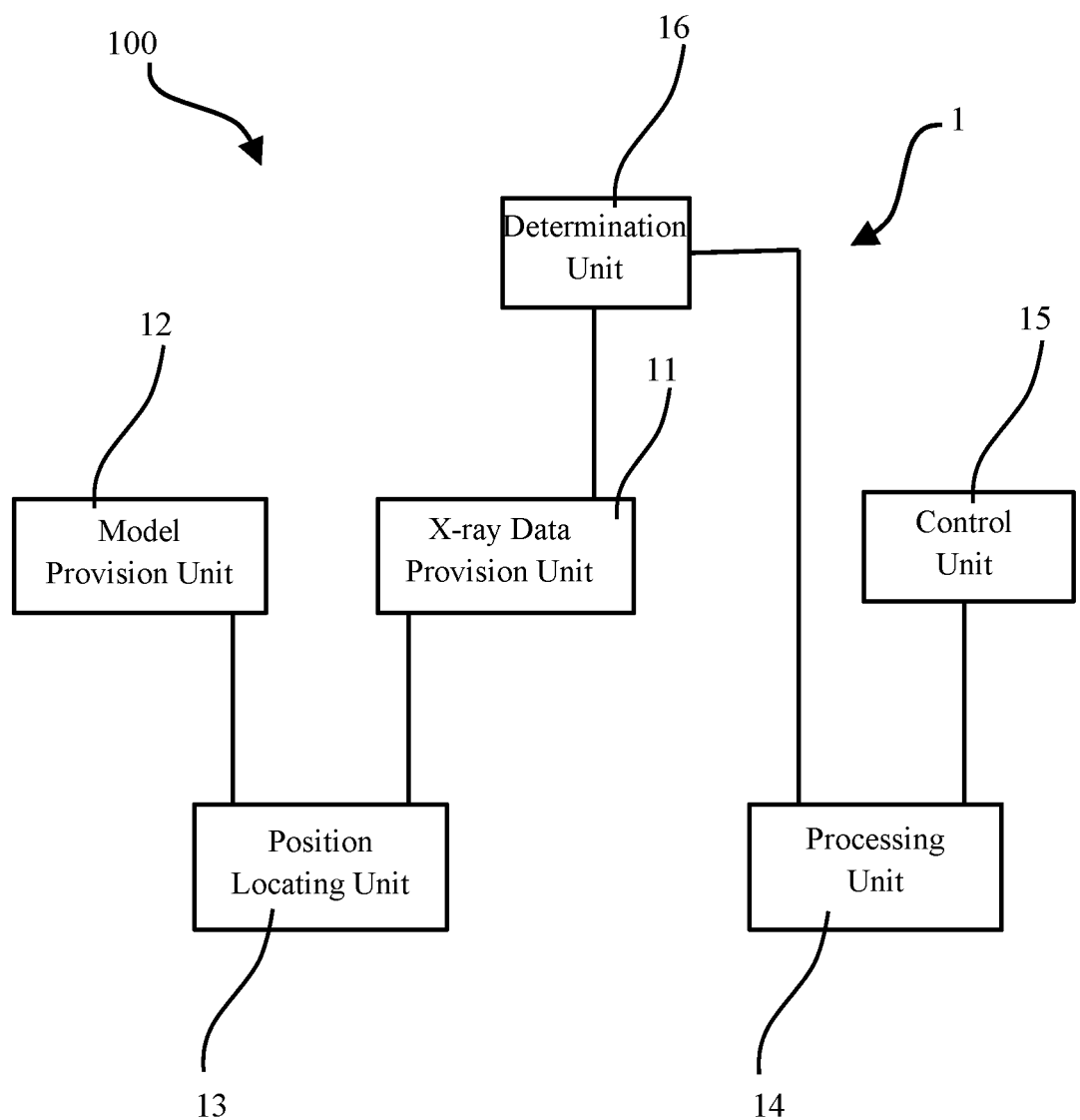
FIG. 1 shows a schematic drawing of an example of a medical imaging system 100 for modifying an imaging of a TEE probe in X-ray data. The medical imaging system 100 comprises the device 1 for modifying an imaging of a TEE probe in X-ray data, a TEE probe and an image acquisition device.

FIG. 1 shows a schematic drawing of an example of a medical imaging system 100 for modifying an imaging of a TEE probe in X-ray data. The medical imaging system 100 comprises the device 1 for modifying an imaging of a TEE probe in X-ray data, a TEE probe and an image acquisition device 102.

The device comprises an X-ray data provision unit 11, a model provision unit 12, a position locating unit 13, and a processing unit 14. The X-ray data provision unit 11 provides X-ray image data comprising image data of a TEE probe and is therefore connected to the image acquisition device. The model provision unit 12 provides model data of the TEE probe. The model data may be a 3D model of the TEE probe. The 3D model of the TEE probe can be a 3D CAD model, a 3D model of TEE probe X-ray attenuation, such as from a CT scan, and/or the like.

The position locating unit 13 locates a position of the TEE probe in the X-ray data based on the model data of the TEE probe. The position locating unit 13 is therefore connected with the X-ray data provision unit 11 and the model provision unit 12.

The processing unit 14 defines a region in a predetermined range adjacent to the TEE probe as reference area. The processing unit 14 is therefore connected with the position locating unit 13. The X-ray data of the reference area may comprise X-ray data of a region around the position of the TEE probe and/or a region within an X-ray transparent portion of the TEE probe.

The processing unit 14 further processes the X-ray data of the reference area into estimated X-ray data of a region occupied by the TEE probe. The processing unit 14 then modifies the X-ray data in the region occupied by the TEE probe based on the estimated X-ray data.

The device 1 for modifying an imaging of a TEE probe in X-ray data according to the present invention enables interventional cardiologists to temporarily modify the TEE probe in the X-ray images without having to move the probe. This enables echocardiographers to continue visualizing structures of interest in the TEE images without interruption, and enables the interventional cardiologists to see the desired structures and devices of interest in the live X-ray images.

The modification of the X-ray data in the region occupied by the TEE probe comprises a hiding of the TEE probe, a translucent or transparent imaging of the TEE probe a reduction to an outline of the TEE probe and/or the like. The translucent or transparent imaging and/or the reduction to an outline may be implemented with a color and/or grey scale to indicate a parameter of interest. Also opacity of the TEE probe in the images can be varied, e.g. depending on TEE probe parameters, as e.g. temperature, pressure, torsion of the various regions/surfaces of the TEE probe etc.

The modification of the X-ray data depends on a user input, a motion of an X-ray data acquisition unit, a motion of an object to be examined and/or the like. Interventional cardiologists may e.g. press a button to temporarily modify the TEE probe in the live X-ray images such that they will then be able to see the structures and devices that were being blocked by the TEE probe. A toggle button can be used to turn the modification on or off during live X-ray image runs.

The device 1 for modifying an imaging of a TEE probe in X-ray data comprises a control unit 15. The control unit 15 controls the modification of the X-ray data in the region occupied by the TEE probe, switches the modification on and off and/or the like. Therefore, the control unit 15 is connected with the processing unit 14.

The device 1 for modifying an imaging of a TEE probe in X-ray data further comprises a determination unit 16 to determine an average data signal and/or noise level of the X-ray data of the reference area. The determination unit 16 may further assign the average data signal and/or noise level to the estimated X-ray data of the region occupied by the TEE probe. The determination unit 16 may further assign an intensity gradient to the estimated X-ray data of the region occupied by the TEE probe. The determination unit 16 is therefore connected to the X-ray data provision unit 11 and the processing unit 14.

Figure 2:
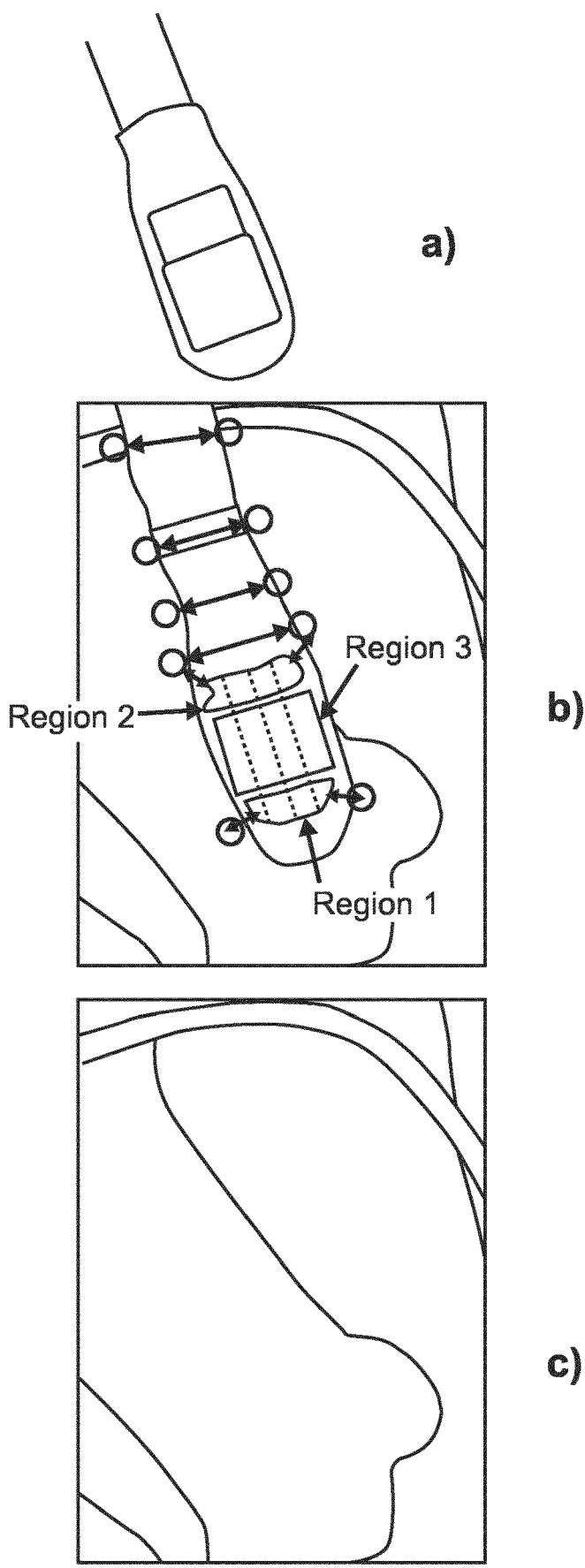
FIG. 2 shows schematic drawings of X-ray images showing a displaying and a hiding of a TEE probe.

FIG. 2 shows schematic drawings of X-ray images showing a displaying and a hiding of a TEE probe. Once activated by a cardiologist, an automated search in X-ray image data begins to locate a TEE probe and its position and orientation. FIG. 2*a* shows an X-ray image displaying a head of the TEE probe. A predesigned computer model of the TEE probe is automatically aligned to the X-ray image of the TEE probe to determine the position and orientation. The computer model of the TEE probe is shown in FIG. 2*a* as overlay over the TEE probe head.

In other words, the TEE probe model is used to determine the TEE probe position and orientation in the X-ray images such that a probe concealment algorithm can be implemented. The computer model of the TEE probe can be expanded to include a part of the TEE probe above the probe head as well. The TEE probe position and orientation determination occurs automatically and very quickly (≈1s) over the course of a very small number of X-ray image frames. The TEE probe alignment functionality can also be used to register X-ray images and TEE images.

FIG. 2b shows the X-ray image displaying the head of the TEE probe to explain a TEE probe modification technique. Regions 1 and 2 in the X-ray image are X-ray transparent parts at the beginning and at the end of the TEE probe head that can be used to hide a radiopaque part of the TEE probe head, which is region 3.

In detail: In addition to the background regions around the perimeter of the TEE probe, the probe head has also two X-ray transparent regions that can also be used to conceal the TEE probe in the X-ray images. These regions are shown as regions 1 and 2 in FIG. 2b. Since the 3D geometry of the probe head is known from the TEE probe model, the geometry of these X-ray transparent regions is also known. Therefore, these X-ray transparent regions can be pre-segmented ahead of time within the probe model. These X-ray transparent regions (and smaller subregions of them) in the probe head can be used to hide the X-ray opaque part of the probe head, shown as region 3.

Regions 1 and 2 can be further sub-segmented and averaged to hide corresponding subregions in region 3. Circular or elliptical subregions along a perimeter of the TEE probe can be averaged and used to hide the perimeter of the TEE probe head along with the region of the TEE probe above the head. A strip of averaged signal and noise between the circles and/or ellipses on opposite sides of the TEE probe can be used to conceal the region of the TEE probe above the TEE probe head.

In detail: Regions 1 and 2 can be broken up into additional subregions in the probe model, as shown by dashed lines in FIG. 2b. Once the probe concealment algorithm is activated, the average image signal and noise level from regions 1 and 2 can be determined in each of these subregions. The part of region 3 contained within a particular subregion can be assigned the average signal and noise level determined from regions 1 and 2 for that particular subregion. The 3D geometry of region 3 is also known in the probe model and can be pre-segmented ahead of time in the model.

Simultaneously with concealing region 3 of the TEE probe, the perimeter of the TEE probe both around and above the TEE probe head should also be concealed. To conceal the perimeter of the TEE probe, small circular or elliptical regions could be defined along the perimeter of the TEE probe, with a diameter of approximately the size of the smallest catheters typically used in interventional cardiology (3F or 1 mm diameter). Since the position and orientation of the TEE probe is known from the TEE probe model being registered to the TEE probe image, these circular and elliptical regions could be automatically generated around the TEE probe perimeter once the TEE probe concealment algorithm is activated.

By delineating circular/elliptical regions on opposite sides of the TEE probe, a strip of image region with signal and noise levels that are the average of the two regions will be overlaid across the TEE probe to conceal it between the two circles or ellipses. These circles or ellipses could also interact with the subregions of regions 1 and 2 on the TEE probe head, to conceal the TEE probe perimeter on the lower part of the TEE probe head. Finally, these circles or ellipses could interact with region 3 after it has been concealed, to conceal the perimeter of the TEE probe around region 3. By using a small enough circle/ellipse size, this will ensure that catheters, guidewires and devices that cross in front of or behind the TEE probe remain visible in the X-ray images after the TEE probe has been concealed.

FIG. 2c shows the modified X-ray image with hidden TEE probe after the TEE probe is concealed. Only e.g. the aortogram, catheters and devices are visible.

Figure 3:
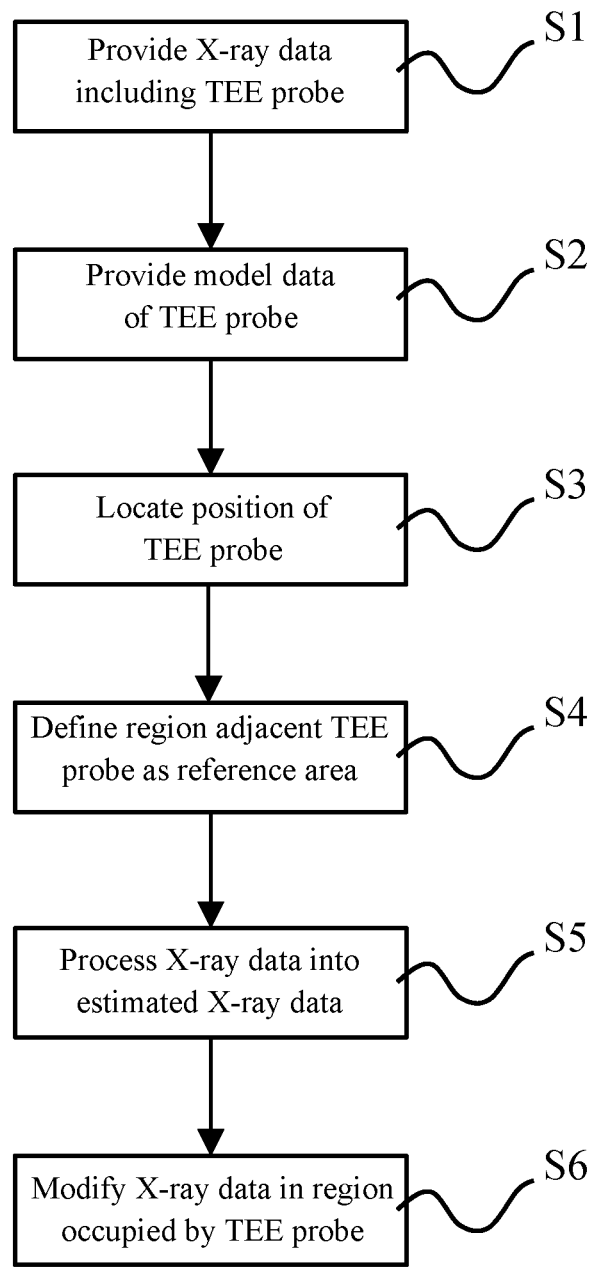
FIG. 3 shows basic steps of an example of a method for modifying an imaging of a TEE probe in X-ray data.

FIG. 3 shows basic steps of an example of a method for modifying an imaging of a TEE probe in X-ray data. The method comprises the following steps, not necessarily in this order:

In a first step S1, providing X-ray data comprising image data of a TEE probe.

In a second step S2, providing model data of the TEE probe.

In a third step S3, locating a position of the TEE probe in the X-ray data based on the model data of the TEE probe.

In a fourth step S4, defining a region in a predetermined range adjacent to the TEE probe as reference area:

In a fifth step S5, processing X-ray data of the reference area into estimated X-ray data of a region occupied by the TEE probe.

In a sixth step S6, modifying the X-ray data in the region occupied by the TEE probe based on the estimated X-ray data.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for modifying an imaging of a transesophageal echocardiography (TEE) probe in X-ray data, comprising:
    an X-ray data provision unit configured to provide the X-ray data comprising image data of the TEE probe;
    a model provision unit configured to provide model data of the TEE probe; and
    a processor configured to: locate a position of the TEE probe in the X-ray data based on the model data of the TEE probe; define a region in a predetermined range adjacent to the TEE probe as a reference area; process the X-ray data of the reference area into estimated X-ray data of a region occupied by the TEE probe; temporarily hide the TEE probe, or translucently or transparently image the TEE probe and/or reduce to an outline of the TEE probe with a color and/or grey scale to indicate a parameter of interest, based on the estimated X-ray data during a C-arm rotational acquisition such that the TEE probe is not present in a 3D reconstructed image volume generated after the C-arm rotational acquisition; and assign an intensity gradient to the estimated X-ray data of the region occupied by the TEE probe.

2. The device according to claim 1, further comprising a controller configured to control a modification of the X-ray data in the region occupied by the TEE probe and to switch the modification on and off.

3. The device according to claim 2, wherein the modification depends on a user input and/or a motion of an X-ray data acquisition unit and/or a motion of an object to be examined.

4. The device according to claim 1, wherein the X-ray data of the reference area comprises X-ray data of a region around the position of the TEE probe and/or a region within an X-ray transparent portion of the TEE probe.

5. The device according to claim 1, wherein the processor is further configured to determine an average data signal and/or noise level of the X-ray data of the reference area and to assign the average data signal and/or noise level to the estimated X-ray data of the region occupied by the TEE probe.

6. The device according to claim 1, wherein the model provision unit is further configured to provide a 3D model of X-ray attenuation or a 3D CAD model.

7. A method for modifying an imaging of a transesophageal echocardiography (TEE) probe in X-ray data, the method comprising:
    a) providing the X-ray data comprising image data of a TEE probe,
    b) providing model data of the TEE probe,
    c) locating a position of the TEE probe in the X-ray data based on the model data of the TEE probe,
    d) defining a region in a predetermined range adjacent to the TEE probe as a reference area,
    e) processing X-ray data of the reference area into estimated X-ray data of a region occupied by the TEE probe,
    f) temporarily hiding the TEE probe, or translucently or transparently imaging the TEE probe and/or reducing to an outline of the TEE probe with a color and/or grey scale to indicate a parameter of interest based on the estimated X-ray data during a C-arm rotational acquisition such that the TEE probe is not present in a 3D reconstructed image volume generated after the C-arm rotational acquisition,
    g). assigning an intensity gradient to the estimated X-ray data of the region occupied by the TEE probe.

8. The method according to claim 7, wherein the X-ray data of the reference area comprises X-ray data of a region around the position of the TEE probe and/or a region within an X-ray transparent portion of the TEE probe.

9. A tangible non-transitory computer readable storage medium having stored therein machine readable instructions when executed by a processor cause the processor to:
    provide X-ray data comprising image data of a transesophageal echocardiography (TEE) probe;
    provide model data of the TEE probe;
    locate a position of the TEE probe in the X-ray data based on the model data of the TEE probe;
    define a region in a predetermined range adjacent to the TEE probe as a reference area;
    process X-ray data of the reference area into estimated X-ray data of a region occupied by the TEE probe;
    temporarily hide the TEE probe, or translucently or transparently image the TEE probe and/or reduce to an outline of the TEE probe with a color and/or grey scale to indicate a parameter of interest based on the estimated X-ray data during a C-arm rotational acquisition such that the TEE probe is not present in a 3D reconstructed image volume generated after the C-arm rotational acquisition; and
    assign an intensity gradient to the estimated X-ray data of the region occupied by the TEE probe.

10. The tangible non-transitory computer readable storage medium according to claim 9, wherein the machine readable instructions when executed by the processor further cause the processor to determine an average data signal and/or noise level of the X-ray data of the reference area and to assign the average data signal and/or noise level to the estimated X-ray data of the region occupied by the TEE probe.

11. The tangible non-transitory computer readable storage medium according to claim 9, wherein the machine readable instructions when executed by the processor further cause the processor to to control and/or to switch on and off the temporarily hiding the TEE probe, translucently or transparently image the TEE probe and/or reduce to an outline of the TEE probe in the region occupied by the TEE probe.

12. The tangible non-transitory computer readable storage medium according to claim 9, wherein the TEE probe comprises a transparent portion arranged at a distal end, or at a proximal end of a head of the TEE probe, or both.

13. The tangible non-transitory computer readable storage medium according to claim 9, wherein the X-ray data of the reference area comprises X-ray data of a region around the position of the TEE probe and/or a region within an X-ray transparent portion of the TEE probe.

14. A medical imaging system, comprising:
 a device, comprising: an X-ray data provision unit; a model provision unit configured to provide model data of a transesophageal echocardiography (TEE) probe; and a processor configured to: locate a position of the TEE probe in X-ray data based on the model data of the TEE probe; define a region in a predetermined range adjacent to the TEE probe as a reference area; process the X-ray data of the reference area into estimated X-ray data of a region occupied by the TEE probe; modify temporarily X-ray data in the region occupied by the TEE probe based on the estimated X-ray data, wherein the X-ray data provision unit is configured to provide the X-ray data comprising image data of a TEE probe; and the processor is further configured to assign an intensity gradient to the estimated X-ray data of the region occupied by the TEE probe; and
 an image acquisition device, wherein the processor is adapted to hide the TEE probe temporarily, translucently or transparently image the TEE probe and/or reduce to an outline of the TEE probe with a color and/or grey scale to indicate a parameter of interest based on the estimated X-ray data during a C-arm rotational acquisition such that the TEE probe is not present in a 3D reconstructed image volume generated after the C-arm rotational acquisition.

15. The medical imaging system according to claim 14, wherein the TEE probe comprises a transparent portion arranged at a distal end, or at a proximal end of a head of the TEE probe, or both.

16. The medical imaging system according to claim 14, wherein the processor is further configured to control and/or to switch on and off the temporarily hiding the TEE probe, translucently or transparently image the TEE probe and/or reduce to an outline of the TEE probe in the region occupied by the TEE probe.

17. The medical imaging system according to claim 16, wherein the temporarily hiding the TEE probe, translucently or transparently image the TEE probe and/or reduce to an outline of the TEE probe depends on a user input and/or a motion of an X-ray data acquisition unit and/or a motion of an object to be examined.

18. The medical imaging system according to claim 14, wherein the X-ray data of the reference area comprises X-ray data of a region around the position of the TEE probe and/or a region within an X-ray transparent portion of the TEE probe.

19. The medical imaging system according to claim 14, wherein the model provision unit is further configured to provide a 3D model of the TEE probe, a 3D model of X-ray attenuation or a 3D CAD model.

20. The medical imaging system according to claim 14, wherein the processor is further configured to determine an average data signal and/or noise level of the X-ray data of the reference area and to assign the average data signal and/or noise level to the estimated X-ray data of the region occupied by the TEE probe.

\* \* \* \* \*